(12) United States Patent
Ongaro et al.

(10) Patent No.: US 10,350,316 B2
(45) Date of Patent: Jul. 16, 2019

(54) AUTOCLAVE

(71) Applicant: NAKANISHI INC., Tochigi (JP)

(72) Inventors: Daniele Giovanni Ongaro, Villa di Serio (IT); Maria Pia Ghilardi, Villa di Serio (IT)

(73) Assignee: NAKANISHI INC., Tochigi (JP)

( * ) Notice: Subject to any disclaimer, the term of this patent is extended or adjusted under 35 U.S.C. 154(b) by 0 days.

(21) Appl. No.: 14/767,361

(22) PCT Filed: Mar. 11, 2014

(86) PCT No.: PCT/IB2014/059624
§ 371 (c)(1),
(2) Date: Aug. 12, 2015

(87) PCT Pub. No.: WO2014/141062
PCT Pub. Date: Sep. 18, 2014

(65) Prior Publication Data
US 2015/0367006 A1 Dec. 24, 2015

(30) Foreign Application Priority Data
Mar. 12, 2013 (IT) .............................. MI2013A0373

(51) Int. Cl.
A61L 2/07 (2006.01)
A61L 2/26 (2006.01)
F22B 1/28 (2006.01)
B01J 3/04 (2006.01)

(52) U.S. Cl.
CPC .................. *A61L 2/07* (2013.01); *A61L 2/26* (2013.01); *F22B 1/285* (2013.01); *A61L 2202/24* (2013.01)

(58) Field of Classification Search
CPC ........................................................ A61L 2/07
USPC ........................................................ 422/292
See application file for complete search history.

(56) References Cited

U.S. PATENT DOCUMENTS

2005/0254803 A1* 11/2005 Ono .................. A23L 3/165
392/405
2007/0297940 A1* 12/2007 Brake .................. A61L 2/07
422/26
2010/0166398 A1* 7/2010 Witt .................. A47L 15/4285
392/441

(Continued)

FOREIGN PATENT DOCUMENTS

EP 0 742 016 A2 11/1996
KR 10-2010-0020842 A 2/2010
WO 96/00534 A1 1/1996

(Continued)

OTHER PUBLICATIONS

International Search Report, dated Jun. 27, 2014, four pages.

*Primary Examiner* — Kevin Joyner
*Assistant Examiner* — Holly M Mull
(74) *Attorney, Agent, or Firm* — Vorys, Sater, Seymour and Pease LLP

(57) ABSTRACT

Provided is an autoclave. The autoclave includes a sterilization chamber, a steam generator including a heat conductor housed in the sterilization chamber and including a vaporization duct for the sterilization fluid, connectors configured to connect the vaporization duct and the sterilization chamber in a fluidic through connection, and a heater configured to heat the heat conductor by vaporizing the sterilization fluid in the vaporization duct.

7 Claims, 2 Drawing Sheets

(56) References Cited

U.S. PATENT DOCUMENTS

2013/0084225 A1* 4/2013 Buczynski ............... A61L 2/07
                                                      422/292

FOREIGN PATENT DOCUMENTS

| WO | 97/48947 A1 | 12/1997 |
| WO | 2013/011388 A1 | 1/2013 |
| WO | WO2013011388 A1 * | 1/2013 |

* cited by examiner

AUTOCLAVE

The present invention relates to an autoclave of the type as recited in the preamble of the first claim.

In particular, the invention relates to a particular device apt to use steam, usually saturated steam, to eliminate micro-organisms (pathogens or non-pathogens or spores and fungi) from medical instruments and, in particular, from medical-dental instruments.

As known, autoclaves sterilise medical instruments (by way of example probe tubes, mirrors, forceps, scalpels) by means of saturated steam at high temperatures and pressures channelled inside a chamber in which the medical instruments to be sterilised are placed.

They therefore comprise a sterilisation chamber inside which the instruments to be sterilised are placed; a supply apparatus suitable to vaporise a sterilisation solution (usually demineralised water) and emit it into the sterilisation chamber; a drainage apparatus for removing the residue (water vapour and condensate) from the sterilisation chamber; and a drying apparatus suitable to dry the instruments at the end of sterilisation.

The supply apparatus comprises a water tank, a steam generator, a plurality of ducts suitable to connect the steam generator to both the tank and the sterilisation chamber; and valves suitable to regulate the circulation of fluid inside said ducts.

In particular, the steam generator is usually place outside the sterilisation chamber and connected thereto by means of ducts.

Alternatively, the steam generator is a resistor inside the chamber which, at the moment of creating steam, is covered by the sterilisation fluid and thus heated so as to vaporise said fluid. In a further alternative, the steam generator is a resistor band placed outside the pressurised recipient.

The prior art described above has several significant drawbacks.

A first significant drawback is represented by the fact that the prior autoclaves do not perform particularly well and, in particular, do not perform good quality sterilisations.

In fact, on account of the heat dispersion of the ducts and the chamber, the steam tends to cool and, in particular to form condensate thus deteriorating the sterilisation process.

To try to resolve such drawback, some autoclaves heat the steam well beyond the temperature needed for sterilisation so as to offset the cooling and/or are fitted with an additional resistor connected externally to the chamber so as to revaporise the condensate formed.

Such solution however results in localised overheating at the point of said resistor apt to deteriorate the structure of the chamber.

Another drawback is the high consumption of autoclaves.

Such aspect is further increased by the need to heat the steam to temperatures well above those effectively needed for the sterilisation and/or the need to vaporise any condensate, that is, to vaporise part of the sterilisation fluid twice.

One significant drawback is represented by the large quantity of sterilisation fluid needed to perform the sterilisation.

Such drawback is particularly evident in autoclaves with a resistor inside the sterilisation chamber where said inner resistor, in order to prevent its breakage by overheating, must always be immersed in the sterilisation fluid.

Another drawback is consequently represented by the slowness of the sterilisation process on account of the slowness with which the autoclaves are able to create the conditions needed to perform sterilisation inside the sterilisation chamber.

A further drawback can be identified in that the autoclaves currently used are of large dimensions.

In particular, this latter drawback is particularly relevant in dental practices where spaces are particularly limited and thus, the presence of an autoclave may get in the doctor's way.

In this situation the technical purpose of the present invention is to devise an autoclave able to substantially overcome the drawbacks mentioned above.

Within the sphere of said technical purpose one important aim of the invention is to provide an autoclave able to ensure high quality, fast sterilisation.

Another important aim of the invention is to obtain an autoclave of compact dimensions and with reduced consumption.

The technical purpose and specified aims are achieved by an autoclave as claimed in the appended claim 1.

Preferred embodiments are described in the dependent claims.

The characteristics and advantages of the invention are clearly evident from the following detailed description of a preferred embodiment thereof, with reference to the accompanying drawings, in which.

Figure 1:
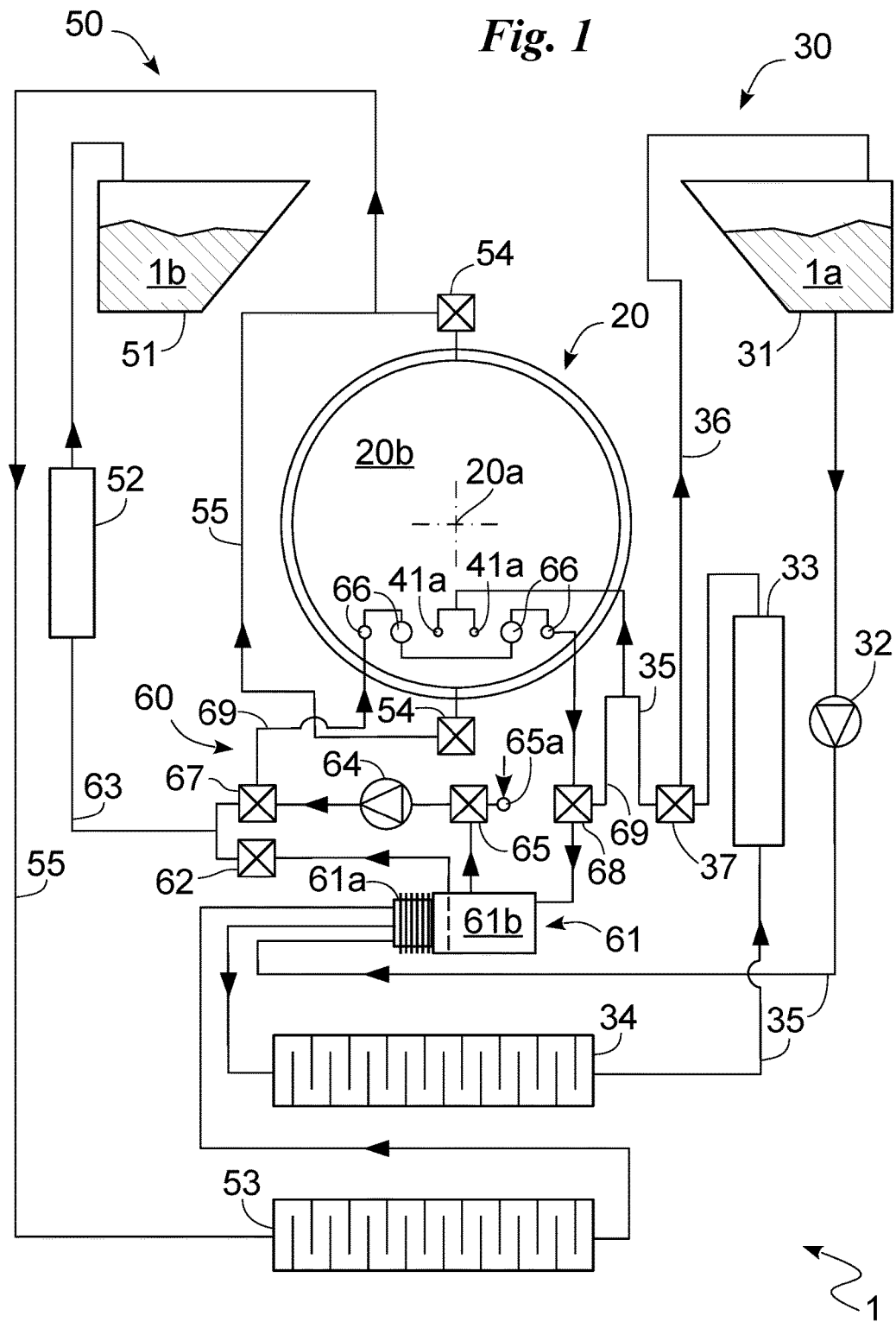
FIG. 1 shows a schematic diagram of the autoclave.

With reference to said drawings, reference numeral 1 globally denotes the autoclave according to the invention.

It is substantially composed of a system for performing the sterilisation of medical instruments and in particular medical-dental instruments and the like, using the vaporisation of demineralised water or other sterilisation fluid 1a.

The autoclave 1, as shown in FIG. 1 mainly comprises, a sterilisation chamber 20 suitable for defining a main extension axis 20a and a watertight space 20b in which to house the medical instruments to be sterilised; a supply system 30 of the sterilisation fluid 1a; a steam generator 40 positioned between the supply system 30 and sterilisation chamber 20 and suitable to vaporise the sterilisation fluid 1a; a drainage system 50 suitable for emptying the drainage fluid 1b from the chamber 20.

Preferably, the chamber 20 has an inner coating 21 suitable to thermally insulate the watertight space 20b from the outside. Said inner coating 21 is made of ceramic or other material suitable to constitute said thermal insulation.

The supply system 30 comprises a filler tank 31 suitable for storing the sterilisation fluid 1a; a supply pump 32 suitable to control the movement of the fluid 1a; a supply filter 33 suitable to filter the sterilisation fluid 1a; a supply cooler 34, appropriately a finned heat exchanger, suitable to lower the temperature of the sterilisation fluid 1a; and supply ducts 35 suitable to permit the sterilisation fluid 1a to cross, in order, the cooler 34, the filter 33 and then reach the steam generator 40.

The supply filter 33 is suitable to reduce the bacterial load of the sterilisation fluid 1a, eliminating bacteria and microorganisms present in the sterilisation fluid 1a, and preferably the conductivity by removing the metals dissolved in the sterilisation fluid 1a.

It thus comprises a first filtering element made of a polymeric material, for example, cellulose acetate, polyamide, polysulfone and polyacrylonitrile, or, an inorganic material, for example, cordierite, borosilicate glass and alumina; and a second filtering element made of resin or other similar material suitable to lower the content of dissolved minerals thereby reducing the conductivity of the fluid treated.

In particular, the first filtering means has a filtering element made of inorganic material and, more particularly, of the membrane type and even more particularly, a porous ceramic-based filter.

The second filtering element comprises a filtering element in resin and, specifically, in ionic exchange resin.

The cooler 34 is suitable to cool the sterilisation fluid 1a bringing it to a temperature substantially below 50° C. and, preferably, to a temperature substantially below 40° C. so as to favour the functioning of the filter 33.

Additionally, the supply system 30 comprises recirculation ducts 36 suitable to conduct the fluid in output from the supply filter 33 into the filler tank 31; and a recirculating valve 37 suitable to direct the sterilisation fluid 1a in output from the supply filter 33 towards the generator 40, through the supply ducts 35 or, alternatively, towards the tank 31 through the recirculation ducts 36.

Appropriately, the recirculation valve 37 has a timer suitable to command the opening/closing of the valve 37 at regular intervals and, more specifically, the entrance or not of the sterilisation fluid 1a into the steam generator 40.

The steam generator 40 comprises at least one heat conductor 41 suitable to house a contact and in particular to house the sterilisation fluid 1a; at least one heater 42 in contact with said heat conductor 41 so as to supply said heat conductor 41 the heat needed to at least partially vaporise the fluid 1a; and connectors 43 suitable to connect the heat conductor 41 and the sterilisation chamber 20.

The heat conductor 41 is advantageously totally housed inside the sterilisation chamber 20 and, specifically, next to the bottom of the sterilisation chamber 20, that is in the area of minimal gravitational potential.

In particular, the heat conductor 41 is connected in the sterilisation chamber 20 without defining spaces/interstices between the chamber 20 and the heat conductor 41. More in particular, the heat conductor 41 is appropriately detachably connected to the sterilisation chamber 20 and to the heaters 42 so as to permit the extraction of the heat conductor 41 only from the chamber 20 without moving the aforesaid heaters 42, that is leaving them in the sterilisation chamber 20.

Figure 2:
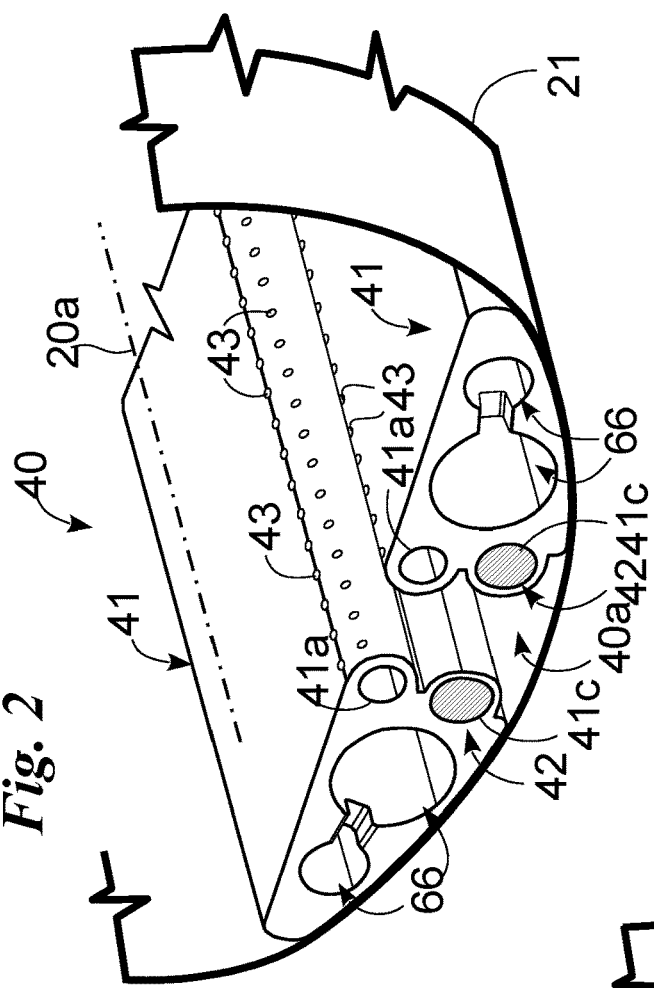
FIG. 2 shows a portion of autoclave according to the invention.

Appropriately, as shown in FIG. 2, the steam generator 40 comprises two heat conductors 41 specular to each other, positioned at the bottom of the sterilisation chamber 20 and suitably distanced so as to define between them a collection channel 40a suitable to collect by gravity and to revaporise the condensate present in the sterilisation chamber 20.

The heat conductors 41 are made of a highly heat conductive material so that the heaters 42 heat the heat conductor 41 in a practically uniform manner. Preferably, they therefore have a heat conductivity substantially greater than 100 W/mK, in particular, substantially greater than 200 W/mK and, even more in particular, substantially at least equal to 250 W/mK.

Preferably, the heat conductors 41 are made of aluminium, copper, bronze or stainless steel.

They are, in addition, appropriately coated with a corrosion-resistant layer suitable for preventing the corrosive action of the fluids 1a and 1b. Said corrosion-resistant layer is made by means of chemical nickel-plating if the conductor 41 is in copper (copper and bronze) or hard anodic oxidation if in aluminium.

Each heat conductor 41 is identifiable in a single body defining at least one vaporisation duct 41a, suitable to receive the sterilisation fluid 1a from the supply ducts 35 and to vaporise said fluid 1a.

The vaporisation duct 41a is of the blind type so that the sterilisation fluid 1a can only come out of it through the connectors 43.

The connectors 43 are identifiable in holes made in the heat conductor 41 having extension axes substantially perpendicular to the extension axis of the duct 41a.

In particular, the extension axis defines an angle of inclination in relation to the gravitational gradient substantially below 45° so as to favour a spontaneous flow of steam from the vaporisation duct 41a to the chamber 20. Said angle is substantially less than 35° and, even more appropriately, substantially parallel to the gravitational gradient.

The generator 40 comprises one or more heaters 42 appropriately arranged in the sterilisation chamber 20 suitable to be housed in the chamber 20 in particular, at least partially housed and, more in particular, substantially totally housed in the heat conductors 41.

Preferably, there are two heaters 42, each of which housed inside a heat conductor 41 and more preferably positioned next to the vaporisation duct 41a. More in particular, the heaters 42 and the vaporisation ducts 41a are positioned at the collection channel 40a and present extension axes substantially parallel to the main extension axis 20a.

The heaters 42 are identifiable in electric resistors appropriately fitted with a heat probe suitable to control the functioning of the electric resistors and thus keep the temperature of the heat conductors 41 substantially between 100-170° C.

Alternatively, the heaters 42 are resistors, preferably heat resistors and more preferably PTC (Positive Temperature Coefficient) heat resistors, that is to say suitable to increase their resistance as the temperature rises and thus to regulate the temperature of the heat conductors 41 without the assistance of heat probes or the like.

The drainage system 50 is suitable to empty the fluid 1b from the chamber 20 and consequently comprises a drainage tank 51 suitable to collect the drainage fluid 1b; a drainage filter 52 substantially analogous to the supply filter 33 and suitable to purify the drainage fluid 1b; a drainage cooler 53, appropriately a finned heat exchanger, suitable to cool the drainage fluid 1b before it reaches the filter 52; drainage valves 54 suitable to control the emptying of the fluid 1b from the chamber 20; and drainage ducts 55 suitable to empty the drainage fluid 1b from the chamber 20 and to cross, in order, the cooler 53, the output filter 52 and then reach the drainage tank 51.

Additionally, the drainage system 50 may advantageously comprise a recovery apparatus 60 suitable to permit a partial re-utilisation of the drainage fluid 1b and, in particular, to use the steam in output from the sterilisation chamber 20. Said recovery apparatus 60 comprises a storage heat exchanger 61 suitable to define a heat exchange between the fluids 1a and 1b and to separate the steam and the condensate composing the drainage fluid 1b; a condensate valve 62 and emptying ducts 63 suitable to control the flow of fluid 1b from the heat exchanger 61 to the drainage filter 52 and a recirculation system suitable to permit an exploitation of the drainage steam or alternatively of air coming from the outside.

The storage heat exchanger 61 is positioned between the output filter 52 and cooler exit 53 and between the supply filter 33 and recirculation valve 37 and comprises a plate cooler 61a suitable to perform the heat exchange between the fluids 1a and 1b; and an accumulator 61b suitable to define a storage space for the drainage fluid 1b in which the steam and condensate separate.

In particular, the plate cooler 61a and the accumulator 61b are appropriately adjacent so that the drainage fluid 1b, stored in the accumulator 61b, defines a heat exchange with the sterilisation fluid 1a circulating in the plate cooler 61a. The recirculation system comprises a vacuum pump 64 suitable to move the fluid in the recirculation system; an input valve 65 suitable to permit the vacuum pump 64 to call back steam from the heat exchanger 61 or air from outside the autoclave 1, one or more hygroscopic spaces 66 housed in the heat conductors 41; a first control valve 67 suitable to permit the steam coming from the vacuum pump 64 to reach the drainage filter 52 or, alternatively, the hygroscopic space 66; a second control valve 68 suitable to direct the fluid coming from the hygroscopic space 66 towards the heat exchanger 61 or the vaporisation ducts 41a; and additional ducts 69 suitable to guide the steam or air into the recirculation system.

The hygroscopic volumes 66 are made in a material having hygroscopic properties consequent to an exothermic reaction such as to emit heat and in particular, dry hot air when they absorbs vapour and subsequently to emit steam when appropriately heated.

Preferably the hygroscopic volumes 66 comprise Zeolite.

In addition they present directions of extension substantially parallel to the main extension axis 20a so as to be substantially parallel to the vaporisation duct 41a and to the heaters 42.

Moreover there are preferably four hygroscopic volumes 66, two inside each heat conductor 41 positioned symmetrically in relation to the collection channel 40a next to the vaporisation ducts 41a and the heaters 42.

The input valve 65 is functionally positioned between the vacuum pump 64 and the heat exchanger 61 and enables the pump 64 to make the steam coming from the accumulator 61b or air coming from outside through an air filter 65a circulate in the system 60.

The air filter 65a is suitable to reduce the bacterial load of the sterilisation fluid 1a, eliminating bacteria and microorganisms present in the air and, consequently is substantially similar to the first filtering element of the supply filter 33 described above.

Figure 3:
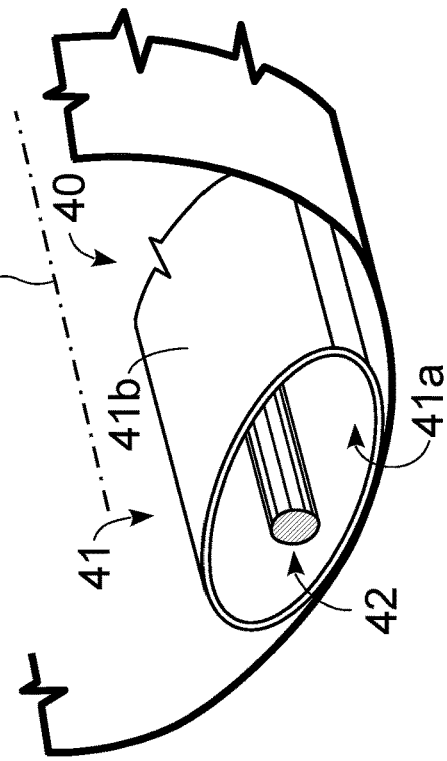
FIG. 3 illustrates an alternative solution to the portion in FIG. 2.

Alternatively to the solution described above providing for two heat conductors 41, as illustrated in FIG. 3, the steam generator 40 comprises a single heat conductor 41 comprising at least one casing 41b, preferably one only, positioned inside the chamber 20 and at the bottom of said sterilisation chamber 20 and made of the aforesaid highly heat conductive material so as to vaporise the possible condensate present in the chamber 20.

The casing 41b defines a single inner cavity identifying the vaporisation duct 41a, suitable to contain the heaters 42 described above and the sterilisation fluid 1a so as to immerse the heaters 42 in the fluid 1a.

In order to favour the immersion of the heaters 42 in the sterilisation fluid 1a, the casing 41b has a circular, appropriately oval cross-section, having a preferred barycentric direction of extension substantially parallel to the main extension axis 20a and extension substantially equal to that of the volume 20b and, additionally, the heaters 42 are positioned substantially along said barycentric direction of extension.

In this case, the connectors 43 are identifiable in a duct, appropriately external to the sterilisation chamber 20 and in a steam valve apt to enable, upon command, a fluid through connection between the vaporisation duct 41a and the chamber 20 and thus, the entry of the steam in the sterilisation chamber 20. The functioning of an autoclave, described above in a structural sense, is as follows.

Initially, the filler tank 31 is filled with a sterilisation fluid 1a, such as water 1a coming from an external mains supply, which is subsequently purified so as to eliminate the bacterial load present in the fluid 1a and reduce its conductivity. In particular, during said purification, the recirculation valve 37 connects the supply filter 33 to the filler tank 31 creating a recirculation of the sterilisation fluid 1a which, thus, after crossing the storage heat exchanger 61, the supply cooler 34 and the supply filter 33, returns to the filler tank 31.

At the same time or alternatively, subsequent to the purification of the sterilisation fluid 1a the sterilisation of the medical instruments takes place.

The operator places the medical instruments inside the sterilisation chamber and commands the heaters 42 to heat the heat conductors 41 bringing them to a temperature substantially comprised between 100-170° C.

In detail, the conductors 41, being in highly heat conductive material, heat evenly and thus so as to begin to heat the chamber 20 and, at the same time, make the hygroscopic volumes 66 regenerate releasing the steam accumulated therein in a previous sterilisation.

Such steam is distanced from the volumes 66 by the vacuum pump 64 which by withdrawing air through the filter 65a and directing it into the hygroscopic volumes 66, guides the steam into the ducts 41a and thus into the sterilisation chamber 20.

The entrance of this steam in the chamber 20 and the vacuum pressure created by the pump 64 in the accumulator 61b empties the fluid 1b from the sterilisation chamber 20. Such drainage fluid 1b then reaches the accumulator 61b from where the condensate, precisely of said drainage fluid 1b, is pushed into the drainage tank 51 through the condensate valve 62.

At this point, the vacuum phase begins, in which the condensate valve 62 is closed while the vacuum pump 64 withdraws steam from the accumulator 61b and directs it into the drainage filter 53, and then, into the drainage tank 51 so as to complete the emptying of the accumulator 61b.

It may be seen how during the regeneration of the volumes 66 and the emptying of the accumulator 61b, the sterilisation fluid 1a, circulating in the supply system 30, passes into the plate cooler 61a and thus cools by conduction the drainage fluid 1b; present in the accumulator 61b.

Once the heat conductors 41 have reached the desired temperature, the vacuum pump 64 is turned off, the drainage valves 54 are closed, while the condensate valve 62 is opened and the valve 65 connects the pump 64 with the outside and the second control valve 68 connects the hygroscopic volumes 66 to the accumulator 61b.

The pressurisation of the sterilisation chamber 20 commences.

In detail, in this step the recirculation valve 37, using the timer, directs the fluid 1a, alternately and at regular intervals, towards the filler tank 31 or the vaporisation ducts 41a so that only a determined amount of sterilisation fluid 1a reaches the generator 40.

The sterilisation fluid then enters the vaporisation ducts 41a of the heat conductors 41, is vaporised and, through the connectors 43, comes out of the ducts 41a into the chamber 20.

Moreover, during such vaporisation, should the sterilisation chamber 20 not be uniformly heated, it absorbs heat from the steam which thus condenses, precipitates by gravity into the collection channel 40a where, coming into contact with the heat conductors 41, it is newly vaporised.

If the conditions of the fluid present in the sterilisation chamber 20 are not as desired the steps of emptying and filling are cyclically repeated until these are achieved.

Once the chamber 20 has achieved the conditions the sterilisation is performed.

After sterilisation is complete, the condensate valve 62 is closed, while the vacuum pump 64 calls back the gas/steam present in the accumulator 61b and sends it through the first control valve 67 to the drainage filter 52 and then to the drainage tank 51.

This action calls back the drainage fluid 1b present in the sterilisation chamber 20 by means of vacuum pressure and through the drainage valves 54 which thus crosses the drainage cooler 53 and passes into the plate cooler 61a.

The drainage fluid 1b lastly reaches the accumulator where it is stored so as to be separated into condensate and steam and to be cooled by the sterilisation fluid 1a circulating in the plate cooler 61a.

When such step is completed, the vacuum pump 64 aspirates air from outside which after being purified/sterilised by the filter 65a is introduced into the hygroscopic volumes 66. Such input of air, together with the heat of the heat conductors 41, makes the hygroscopic volumes 66 regenerate completely and thus release steam which is pushed into the ducts 41a.

Additionally, such passage of air lowers the temperature of the heat conductors 41 which thus identify an area of the chamber 20 at reduced temperature, that is to say a cold point which favours the condensation of the steam present in the chamber 20 and consequently the drying of the instruments.

Once the hygroscopic volumes 66 are regenerated the drying of the medical instruments is completed by means of a jet of hot air.

In detail, the pump 64, by means of the input valve 65, calls back steam from the accumulator 61b and brings it to the hygroscopic volumes 66 which fill, releasing heat which heats the chamber 20 through the heat conductors 41 and dry air which is introduced back into the chamber through the connectors 43 so as to dry the medical instruments.

Once such operation has been completed, the operator removes the medical instruments from the autoclave 1, and then proceeds with another sterilisation. The invention achieves some important advantages.

A first important advantage is the particularly high quality sterilisation which can be achieved with the autoclave 1.

Such aspect is achieved by the presence of the heat conductors 41 in the sterilisation chamber 20 which, by creating steam directly in the chamber 20 prevents heat dispersion and thus prevents the steam from cooling and forming condensate.

In particular, such aspect is additionally prevented by the arrangement of the heat conductors 41 on the bottom of the chamber 20 and in particular, by the creation of the collection channel 40a inside which any condensate accumulates permitting said heat conductors to re-vaporise it.

Another advantage of the autoclave 1 is therefore the fact that, the sterilisation fluid 1a present in the chamber is always high quality and, in particular, at an ideal sterilisation temperature.

Another advantage is given by the particular arrangement of the hygroscopic volumes 66 which, being housed in the heat conductors 41 and thus in the sterilisation chamber 20 make it possible to exploit their absorption phase both to heat said chamber and to generate dry hot air.

Moreover, this arrangement of the hygroscopic volumes 66 makes it possible to exploit the heating of the heat conductors both to generate steam and to regenerate the hygroscopic volumes 66.

Such particular exploitation of the hygroscopic volumes 66 has been innovatively achieved in part thanks to the heat exchanger 61 which thanks to the presence of the accumulator 61b defines a collection point for the waste fluid 1b suitable to permit the separation of the condensate and steam and thus, the particular exploitation of the steam through the volumes 66.

A further advantage given by the presence of the heat exchanger 61 and the coolers 34 and 53 is the possibility of having the fluids 1a and 1b at an ideal temperature when they reach the filters 33 and 52.

One advantage is the fact that, the autoclave 1, by having the steam generator 40 inside the chamber 20 is particularly compact compared to the prior sterilisers and thus suitable to allow better use of the doctor's available space.

Another advantage is given by the presence of the timer which enables the recirculation valve 37 to send at regular intervals a determined quantity of sterilisation fluid 1a to the generator 40 optimising the vaporisation of the sterilisation fluid 1a.

Such aspect is further given by the definition of the blind vaporisation ducts 41a which allow the sterilisation fluid 1a to stay inside them and thus to be completely vaporised and by the fact that should the sterilisation fluid 1a come out of them through the connectors 43 it falls by gravity into the collection channel 40a where it is vaporised by the heat conductors 41.

Another advantage is given by the presence of the heat conductors 41 and, in particular, by their arrangement on the bottom of the chamber 20 making it possible to keep the condensate present in said chamber heated even during the depressurisation of the chamber 20.

One advantage is given, as described in the functioning of the autoclave 1, by the possibility of introducing sterile and heated dry air into the sterilisation chamber 20 which makes it possible to dry the medical instruments in an extremely rapid, safe manner.

One important advantage is given by the possibility of removing the heat conductors 41 from the sterilisation chamber 20 to permit easy cleaning of the autoclave 1.

Moreover, such operation is facilitated by the fact that the heaters 42, remaining permanently connected to the chamber 20, remain still during the extraction and insertion of the conductors 41 and thus guide the movement thereof.

Another important advantage is the use of the casing 41b which, being suitable to contain within it sterilisation fluid 1a at high temperatures, defines a heat source for the sterilisation chamber 20, favouring the heating thereof.

Such heating of the chamber 20 proves particularly advantageous both during drying of the instruments by favouring the heating of the air present in the autoclave and during the sterilisation of the instruments vaporising the condensate which has possibly formed and preventing a dangerous cooling of the sterilisation chamber 20.

Another advantage of no less importance is the possibility of using air coming from outside to rapidly cool the sterilisation chamber 20 and then, perform a vacuum test of the autoclave 1 at any moment without particular expectations.

Variations may be made to the invention described herein without departing from the scope of the inventive concept.

All the elements as described and claimed herein may be replaced with equivalent elements and the scope of the invention includes all other details, materials, shapes and dimensions.

The invention claimed is:

1. An autoclave for performing the sterilisation of medical instruments, comprising:
   a sterilisation chamber;
   a steam generator configured to vaporise a sterilisation fluid for said sterilisation chamber, said steam generator comprising at least one heat conductor housed in said sterilisation chamber, positioned in correspondence with the bottom of said sterilisation chamber, being configured to come into contact with said sterilisation fluid without defining spaces or interstices between said sterilization chamber and said heat conductor, and comprising a vaporisation duct for the sterilisation fluid;
   connectors configured to connect said vaporisation duct and said sterilisation chamber in a fluidic through connection; and
   at least one heater housed in said vaporisation duct, and at least partially housed in said at least one heat conductor, so as to heat said heat conductor by vaporising at least partially said sterilisation fluid in said vaporisation duct.

2. The autoclave of claim 1, wherein said at least one heater is substantially completely housed in said at least one heat conductor.

3. The autoclave of claim 1, wherein said steam generator comprises two of said at least one heat conductors.

4. The autoclave of claim 3, wherein said heat conductors are distanced from each other defining a collection channel configured for receiving condensation by gravity.

5. The autoclave of claim 1, as claimed in wherein said sterilisation chamber is configured to define an airtight volume and comprises an inner coating configured to thermally insulate said airtight volume.

6. The autoclave of claim 1, further comprising at least one hygroscopic volume housed in said at least one heat conductor.

7. The autoclave of claim 6, wherein said at least one hygroscopic volume comprises Zeolite.

* * * * *